United States Patent
Chandramowli et al.

(10) Patent No.: US 10,729,628 B2
(45) Date of Patent: Aug. 4, 2020

(54) TYROSINASE INHIBITORS

(71) Applicant: Conopco, Inc., Englewood Cliffs, NJ (US)

(72) Inventors: Ganesh Chandramowli, Bangalore (IN); Gurunath Ramanathan, Uttar Pradesh (IN); Sreenivasa Thimmaiah, Kadur (IN); Garima Tripathi, Uttar Pradesh (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/065,202

(22) PCT Filed: Nov. 23, 2016

(86) PCT No.: PCT/EP2016/078566
§ 371 (c)(1),
(2) Date: Jun. 22, 2018

(87) PCT Pub. No.: WO2017/108316
PCT Pub. Date: Jun. 29, 2017

(65) Prior Publication Data
US 2019/0008737 A1 Jan. 10, 2019

(30) Foreign Application Priority Data
Dec. 24, 2015 (EP) ..................... 15202739

(51) Int. Cl.
| | | |
|---|---|---|
| A61K 8/42 | (2006.01) | |
| A61Q 19/02 | (2006.01) | |
| A23L 33/10 | (2016.01) | |
| A61K 31/357 | (2006.01) | |
| A61K 8/39 | (2006.01) | |
| A61K 38/06 | (2006.01) | |
| A23L 3/3508 | (2006.01) | |
| A23L 3/349 | (2006.01) | |
| A23L 3/3517 | (2006.01) | |

(52) U.S. Cl.
CPC ............ *A61K 8/42* (2013.01); *A23L 3/349* (2013.01); *A23L 3/3508* (2013.01); *A23L 3/3517* (2013.01); *A23L 33/10* (2016.08); *A61K 8/39* (2013.01); *A61K 31/357* (2013.01); *A61K 38/06* (2013.01); *A61Q 19/02* (2013.01); *A23V 2002/00* (2013.01)

(58) Field of Classification Search
None
See application file for complete search history.

(56) References Cited

U.S. PATENT DOCUMENTS

| 5,965,524 A | 12/1999 | Burke, Jr. et al. | |
|---|---|---|---|
| 9,242,991 B2 * | 1/2016 | Hu | C07D 498/04 |
| 9,456,972 B2 | 10/2016 | Choi | |
| 9,795,550 B2 * | 10/2017 | Hood | A61K 8/49 |
| 2007/0231284 A1 | 10/2007 | Pinel et al. | |
| 2010/0272660 A1 | 10/2010 | Malle | |
| 2011/0236815 A1 | 9/2011 | Veregin et al. | |
| 2014/0309173 A1 | 10/2014 | Dreher | |

FOREIGN PATENT DOCUMENTS

| CN | 103130791 | 6/2013 |
|---|---|---|
| CN | 103497985 | 1/2014 |
| DE | 10306452 | 9/2004 |
| EP | 2295403 | 3/2011 |

(Continued)

OTHER PUBLICATIONS

Written Opinion in PCTEP2016078566; dated Nov. 30, 2017.

(Continued)

*Primary Examiner* — Brian J Davis
(74) *Attorney, Agent, or Firm* — Foley & Lardner LLP

(57) ABSTRACT

Disclosed is a compound of the formula (I), (IIA) or (IIB) for use to treat hyperpigmentation of human skin by inhibiting the activity of human tyrosinase in an animate substrate which is human skin containing human tyrosinase. (I) (IIA) (IIB) where: X is oxygen, sulphur, selenium or tellurium; R is —OH, alkyl, aryl or peptide group: R1 is —OH, alkyl, aryl or peptide group; R2 is —OH, alkyl, aryl or peptide group; n is an integer from 2 to 5; m is an integer from 2 to 4 and p is an integer from 2 to 4.

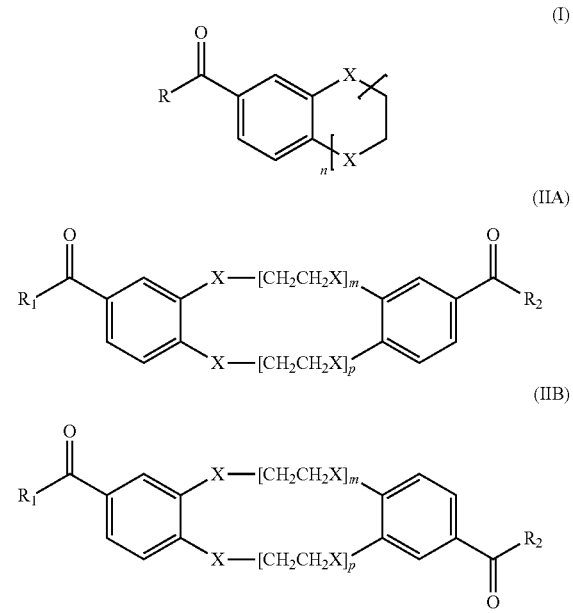

8 Claims, No Drawings

(56) References Cited

FOREIGN PATENT DOCUMENTS

| | | |
|---|---|---|
| FR | 2921828 | 4/2009 |
| JP | 5170636 | 12/1991 |
| JP | 5170637 | 12/1991 |
| JP | 6345797 | 6/1993 |
| JP | 2002284668 | 10/2002 |
| JP | 2009062363 | 3/2009 |
| KR | 20100092150 | 8/2010 |
| WO | WO0208174 | 1/2002 |
| WO | WO2004046167 A2 | 6/2004 |
| WO | WO2004046167 A3 | 7/2005 |
| WO | WO2007101882 | 9/2007 |
| WO | WO2011125040 | 10/2011 |
| WO | WO2011126163 | 10/2011 |
| WO | WO2012013136 | 2/2012 |
| WO | WO2012121428 | 9/2012 |
| WO | WO2013063615 | 5/2013 |
| WO | WO2013073763 | 5/2013 |
| WO | WO2014080376 | 5/2014 |

OTHER PUBLICATIONS

Search Report and Written Opinion in PCTEP2016078566; dated Feb. 16, 2017.
Broos et al.; Enhancement of tyrosinase activity by macrocycles in the oxidation of p-cresolin organic solvents; Journal of the Chemical Society Perkin Transactions ; 1996; pp. 1415-1417; XP055342397; No. 12.
Anca Paun et al.; Synthesis and microbiological evaluation of several benzocaine derivatives; C.R. Chimie; 2013; pp. 665-671; XP055247941; vol. 16, No. 7; Elsevier.
U.Z. Mirkhodjaev et al.; On the Mechanism of Action of Dibenzo-18-crown-6 Diacyl-Derivatives on Malignant Tumors; Journal of Inclusion Phenomena and Macrocyclic Chemistry; 2005; pp. 191-196; XP019248823; vol. 53, No. 3; Springer.
K.M. Valikhanov et al.; Synthesis of New Derivatives Based on Benzo-Crown Ethers and Some Natural Amines; Chemistry of Natural Compounds; 1998; pp. 613-615; XP055247756; vol. 34, No. 5.
D.V. Kuznetsov et al.; Synthesis, Extraction, and Transport properties of Dibenzo-18-crown-6 Modified with the Fragments of 2-Amino-1,3,4-thiadiazol and Kojic Acid; Russian Journal of General Chemistry; 2008; pp. 1924-1928; XP055251973; vol. 78, No. 10.
Search Report & Written Opinion in EP15202739; dated Mar. 7, 2016.
Gierlli et al; Inhibition of Polyphenol Oxidases Activity by Various Dipeptides; Journal of Agricultural and Food Chemistry,; 2004; pp. 2741-2745; vol. 52.
Botta, et al.; Selective Synthesis of DOPA and DOPA Peptides by Native; ChemPlusChem; 2013; pp. 325-330; 78.
Ugras, et al.; Experimental, Theoretical and Biological Activity Study on the Acyl-Substituted; Journal of Includion Phenomena and Macrocyclic Chemistry; 2006; pp. 159-165; 55.
Na-Wan Hsiao, et al.; Serendipitous Discovery of Short Peptides from Natural Products as Tyrosinase Inhibitors; Journal of Chemical Information and Modeling; 2014; pp. 1-13.

* cited by examiner

US 10,729,628 B2

TYROSINASE INHIBITORS

FIELD OF THE INVENTION

The invention relates to compounds that inhibit the activity of human and mushroom tyrosinase, and to compositions containing such compounds.

BACKGROUND OF THE INVENTION

Tyrosinase is a critical target to modulate pigmentation of skin. It is possible to lighten the colour of human skin by use of cosmetic or pharmaceutical compositions containing tyrosinase inhibitors. Tyrosinase is a copper bound enzyme and inhibitors that target this enzyme are potential skin lightening agents. The cosmetic and pharmaceuticals industry has always been interested in compounds which inhibit the activity of tyrosinase.

Consumers of cosmetic compositions desire even skin tone, no or minimal age spots, absence of hyperpigmentation and overall a lighter skin tone. There are biological actives that reduce the activity of melanocyte cells present in human skin. Melanocytes are present in the basal layer of epidermis and they produce melanin and export it, in small export vesicles, called melanosomes, to neighbouring keratinocytes. Compounds that reduce synthesis melanin when topically applied to the skin can lighten the skin over a period. Tyrosinase is one of the many targets to regulate production of melanocytes. However, some of the effective inhibitors of tyrosinase are not too safe and they may cause melanocyte cell death, permanent depigmentation, irritation or allergic reactions.

Therefore, there is need for safe and effective inhibitors of tyrosinase.

K M Valikhanov et. al. Synthesis of New Derivatives based on benzo-crown ethers and some natural amines" Chemistry of Natural Compounds, Vol 34, No. 4, 1 Jan. 1998. pages 613-615 discloses the use of certain crown ether derivatives.

Mirkhodjaev U Z et. al: On the Mechanism of Action of Dibenzo-18-Crown-6-diacyl derivatives on Malignant Tumours", Journal Of Inclusion Phenomenon And Macrocyclic Chemistry, 53(3), 1 Nov. 2005, pages 191-196 discloses the use of a crown ether in cancer treatment.

U.S. Pat. No. 5,965,524 A (Burke et. al, 1999) discloses analogs of viscosin, pharmaceutical compositions thereof and to methods of using viscosin and crown ether analogs thereof as biosurfactants and as antibacterial, antiviral and antitrypanosomal therapeutic compounds. In particular, compositions that inhibit thegrowth of the pathogens *Mycobacterium tuberculosis,*

WO02/08174 A1 (Riley Patrick) discloses novel mono- and dihydroxy phenylethylamine derivatives useful in treating melanoma. The compounds are prodrugs which are inactive until metabolised by enzymes expressed by host melanoma cells. The invention allows a greater amount of active agent to be used while reducing systemic side effects.

EP 2295403 A1 (Corum Inc, 2011) discloses compounds with a carboxyl acid group and an amide group also containing the tertiary amino groups. The carboxyl acid group having a partial negative charge attracts the tertiary amino group to form a quaternary ammonium salt structure. These compounds have a mushroom tyrosinase-inhibition effect and have the potential to use in the cosmetics for skin whitening.

Anca Paun et. al: "Synthesis and microbiological evaluation of several benzocaine derivatives". Compus Rendus—Chimie, Vol 16 no. 7. 1 Jul. 2013, pages 665-671 discloses crown ether derivatives of benzocaine, its antimicrobial and antioxidant properties.

CN 103130791 A (Jiangsu et. al, 2013) discloses crown ether derivatives of benzamide and their anticancer properties.

D V Kutnetsov et. al: Synthesis, extraction and transport properties of dibenzo-18-crown-6 modified with the fragments of 2-amino-1,3,-thiadiazol and kojic acid" Russian Journal Of General Chemistry, 78(10), 1 Oct. 2008, 1924-1928 discloses certain crown ethers in the preparation of new antibacterial agents.

FR2921828 A1 (Oreal, 2009) discloses a cosmetic or pharmaceutical composition comprising a polycondensate obtained by the reaction of one or more polyols comprising hydroxyl groups.

While human tyrosinase has been the primary subject of research, others like mushroom tyrosinase are also equally important. Mushroom tyrosinase is similar to plant polyphenol oxidases. These forms are present in food products and beverages and believed to be responsible for darkening or browning. Therefore, inhibition of mushroom tyrosinase is also important for the foods and refreshments industry.

We have now found that certain crown ethers have the ability to inhibit the activity of tyrosinase, human as well as mushroom. Such crown ethers are potential actives for cosmetic compositions as well as food and beverage compositions for inhibitory activity of tyrosinase.

SUMMARY OF THE INVENTION

In accordance with a first aspect is disclosed a compound of the formula (I) or (II) for use as claimed in claim 1.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

All references to the term/expression wt % or % by weight, shall mean percentage by weight of the composition, except where indicated otherwise.

DETAILED DESCRIPTION OF THE INVENTION

Crown ethers comprise a ring of repeating ether groups and are considered to be oligomers of ethylene oxide [(—$CH_2CH_2O$—)$_n$]. They contain a central cavity, which can accommodate cations (the well-known case being potassium/sodium) in the ring interior, coordinating with e.g., oxygen atoms.

Metal ions (inorganic cations) play crucial role in various biological processes. The formation of melanin pigment is via the activity of tyrosinase. Similar reactions play a part in plant derived materials, especially in the context of browning of food/beverage compositions. Without wishing to be bound by theory, it is believed that copper chelators can inhibit the activity of tyrosinase and therefore such compounds are suitable for use in skin lightening products and for food products where the activity of tyrosinase needs to be controlled.

Melanin is produced by a complex set of reactions within the melanocyte involving, at a basic level, the enzyme tyrosinase and the aminoacid L-tyrosine. It is well known that tyrosinase is an essential component of melanin synthesis. Tyrosinase catalyzes the conversion of L-tyrosine to dopaquinone via L-DOPA (L-3,4-dihydroxyphenylalanine) as an intermediate. Dopaquinone undergoes further conversion to form melanin. As disclosed earlier, a need exists for novel methods and compositions to inhibit tyrosinase activity.

Disclosed in accordance with the first aspect of the invention is a compound of the formula (I), (IIA) or (IIB) for use to treat hyperpigmentation of human skin by inhibiting the activity of human tyrosinase in an animate substrate which is human skin containing tyrosinase.

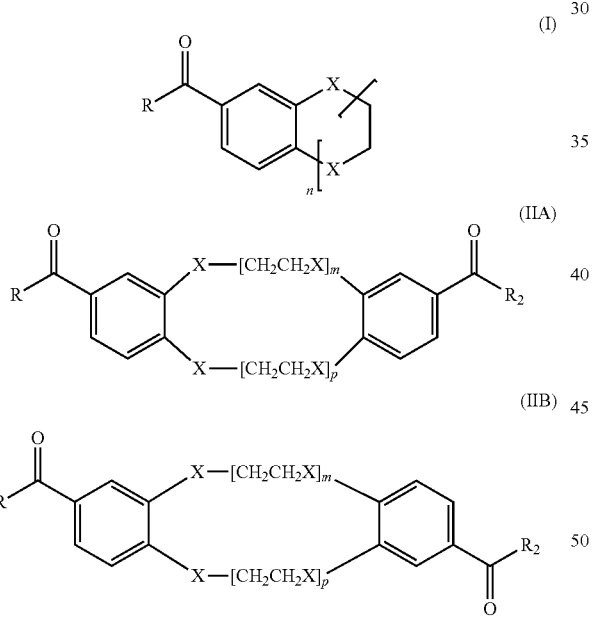

where:
X is oxygen, sulphur, selenium or tellurium; R is —OH, alkyl, aryl or peptide group: $R_1$ is —OH, alkyl, aryl or peptide group; $R_2$ is —OH, alkyl, aryl or peptide group; n is an integer from 2 to 5; m is an integer from 2 to 4 and p is an integer from 2 to 4.

Compounds of the formulae (I) generally belong to the class of benzo crown ethers. On the other hand, the compounds of the formula (IIA) and (IIB) belong to the class of dibenzo crown ethers. (IIA) and (IIB) are positional isomers.

The special technical feature common between formulae (I), (IIA) and (IIB) is the benzo crown ether part, which is believed to be responsible for inhibition of tyrosinase.

Formulae (I), (IIA) and (IIB) may be considered alternatives having a common activity, which is the inhibition of the activity of tyrosinase, mushroom as well as human. The formulae (I), (IIA) and (IIB) also contain structural elements of the benzo crown ether nucleus. The compounds represented by (I), (IIA) and (IIB) share a common chemical structure which occupies a large portion of their structures, or, alternatively, it may also be said that the commonly shared structure constitutes a structurally distinctive portion.

Although it is possible to have compounds which contain sulphur or tellurium, it is preferred that in each said formula, each said X is oxygen.

It is preferred that in formula (I), the R is —OH. In other words, the substituent is a carboxylic acid group.

Alternatively, in said formula (I), said R is an amide group of the formula (III), where the carbonyl carbon in said formula (I) is bonded to the nitrogen atom of the formula (III) which is indicated by the arrow.

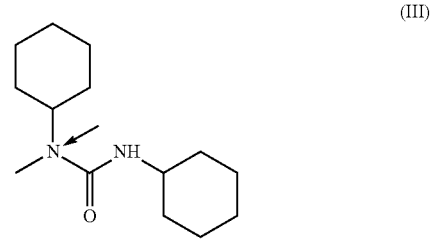

In the case of each of the compounds of the formulae (IIA) and (IIB), it is preferred that at least one of the $R_1$ or $R_2$ is —OH. In other words, at least one substituent is a carboxylic group. Alternatively, there are two carboxylic groups, in which case, each one of $R_1$ and $R_2$ is —OH group.

Alternatively, in the case of the compound of formula (IIA) and (IIB), it is preferred that least one of the $R_1$ or $R_2$ is a amide group of the formula (IV), where the carbonyl carbon in said formula (IIA or IIB) is bonded to the nitrogen atom of the formula (IV) which is indicated by the arrow.

(IV)

Table 1 has some exemplary compounds particularly preferred for use in accordance with the invention.

TABLE 1

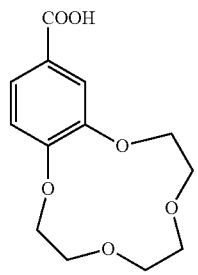 [SMILES: O=C(O)c1ccc2c(c1)OCCOCCOCCO2]

(a)

TABLE 1-continued

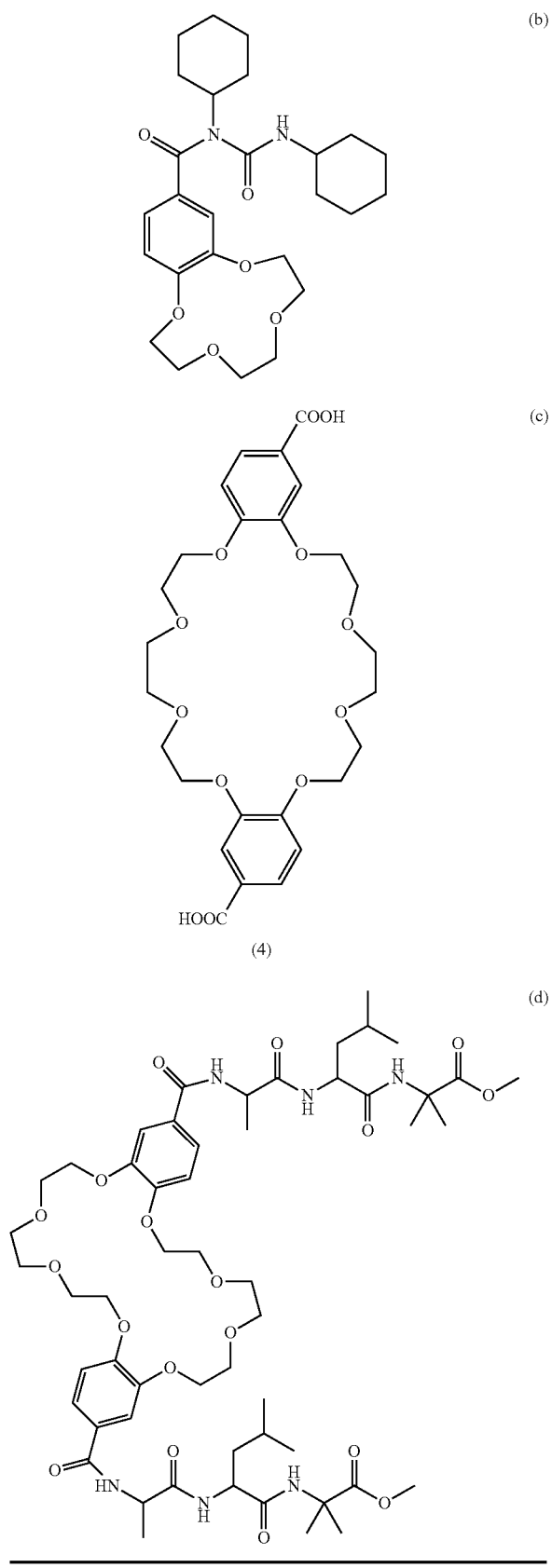

Compounds (a) and (b) are exemplary embodiments of the compound of the general formula (I).

In the case of (a), each X is oxygen; R is —OH and n is equal to 3.

In the case of compound (b), each X is oxygen; n is equal to 3 and R is:

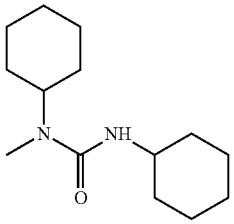 [SMILES: CN(C(=O)NC1CCCCC1)C1CCCCC1]

In the case of compound (c), each X is oxygen, R1 is —OH; R2 is —OH, m is equal to 3, p is equal to 3.

Similarly, in the case of compound (d), each X is oxygen, m is equal to 3, p is equal to 3 and each one of R1 and R2 is:

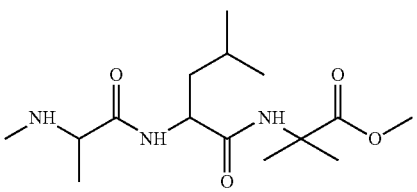

The Tyrosinase

The tyrosinase is either human or mushroom tyrosinase. The animate substrate is human skin.

Alternatively, the compound is used to inhibit the activity of tyrosinase in an inanimate substrate which is a food or beverage composition.

In accordance with another aspect of the invention is disclosed the non-therapeutic use of a compound of the formula (I), (IIA) or (IIB) to inhibit the activity of tyrosinase in an animate or inanimate substrate.

The use is for non-therapeutic applications to inhibit the activity of human tyrosinase in an animate substrate which is human skin containing said human tyrosinase, more preferably for cosmetic applications such as in cosmetic creams and lotions which are available in stores and supermarkets and which are used by many people who desire a beautiful, even-tone and blemish-free complexion. Persons skilled in the art know the differences between medical and cosmetic use. Cosmetic compositions are used to maintain the condition of skin or to beautify it, whereas medical compositions are useful to mitigate a medical condition.

Alternatively, the use is for therapeutic applications as in treatment of any medical condition such as hyperpigmentation.

In another aspect the invention provides a method of treat hyperpigmentation of human skin by inhibiting the activity of human tyrosinase in an animate substrate which is human skin, by contacting said substrate with a compound of formula (I), (IIA) or (IIB). Further, preferably the method is non-therapeutic. Alternatively, it is of therapeutic nature as explained earlier.

In accordance with yet another aspect is disclosed a composition comprising:
(i) 0.01 to 10% by weight a compound of the formula (I), (IIA) or (IIB); and,
(ii) a carrier,
for use to treat hyperpigmentation of skin by inhibiting the activity of tyrosinase in an animate substrate containing said human tyrosinase which is human skin.

In accordance with yet another aspect is disclosed use of a compound of the formula (I), (IIA) or (IIB) to inhibit the activity of mushroom tyrosinase in a food or a beverage composition.

In accordance with yet another aspect is disclosed the use of a compound of the formula (I), (IIA) or (IIB) in the preparation of a food or beverage composition to inhibit the activity of mushroom tyrosinase in said composition.

Methods of inhibiting tyrosinase activity may involve application of the aforementioned composition. The composition is applied to a substrate in need of tyrosinase inhibition. Substrates in need of tyrosinase inhibition include any substrate containing tyrosinase which an individual selects for inhibition. In certain embodiments, the animate substrate is a human skin surface. A suitable skin surfaces include facial skin surfaces, hand and arm skin surfaces, foot and leg skin surfaces, and neck and chest skin surfaces. In certain embodiments, a particular area or areas of the skin surface may be selected for tyrosinase inhibition. In one embodiment, the area may be the facial skin surface including the forehead, perioral, chin, periorbital, nose, and/or cheeks.

The area on the skin surface could be a hyperpigmented spot or other area with increased melanin production. Hyperpigmented spots may be identified by the user or a third party such as a dermatologist, cosmetician, or other caregiver. Identification may be by visual inspection of the skin for hyperpigmented spots in need of treatment based on size and/or colour. Commercially available imaging devices such as SIAscope® V may be used to identify hyperpigmented spots.

The composition may be applied and left on the substrate for a sufficient time or may be repeatedly applied a sufficient number of times to inhibit the activity of tyrosinase. In certain embodiments, the contact time is greater than about 1 hour, 2 hours, 6 hours, 8 hours, 12 hours, or 24 hours. The contact time is time from application of the composition until the composition is removed. In certain embodiments, the composition may be removed by rinsing or washing the substrate. When human skin surface is the animate substrate, the composition may be removed by washing or rinsing the skin. The treatment period may involve a single application or multiple applications. The composition may be applied at least once daily. In other embodiments, the composition is applied at least twice daily. Multiple applications may occur over the course of at least about one week. Alternately, the treatment period may last more than about 4 weeks or more than about 8 weeks. In certain embodiments, the treatment period will extend over multiple months (i.e., 3 to 12 months) or multiple years. In the case of cosmetic composition, the composition may be applied daily for prolonged period.

Where such compositions are cosmetic compositions, they are applied to maintain the tone, colour or texture of the skin. In such case, the use generally is prolonged involving daily application of the composition. The user may thereafter continue application.

Other Ingredients:
When the composition in accordance with the invention is cosmetic composition, it preferably comprises one or more of fragrance, skin lightening compound, surfactant, organic sunscreen, inorganic sunscreen, extender pigment and preservative.

The skin lightening compound may be selected from the group consisting of niacinamide, resorcinols, kojic acid, retinol, retinyl esters including retinyl palmitate, 12-hydroxystearic acid, lactic acid, ascorbic acid, glabradin, dioic acids including octadecenedioic acid and azeleic acid, resveratrol, ascorbyl phosphate, ascorbyl palmitate, acetyl glucosamine, calcium pantothenate, alpha arbutin, climbazole, pitera extract, soybean extract, undecylenoyl phenylalanine, aqueous extract of bearberry and mixtures thereof.

The resorcinol may be selected from the group consisting of 4-ethyl resorcinol, 4-hexyl resorcinol, 4-isopropyl resorcinol and phenylethyl resorcinol. It is particularly preferred that the skin-lightening compound is a non-tyrosinase inhibiting skin-lightening compound. The composition could comprise 0.0001 to 10, preferably 0.01 to 2, most preferably 0.1 to 1% by weight of the skin lightening compound. Sunscreens include those materials which block harmful ultraviolet light. Preferred sunscreens are the derivatives of p-aminobenzoic acid (PABA), cinnamate and salicylate. For example, avobenzophenone (Parsol® 1789), octyl methoxycinnamate and 2-hydroxy-4-methoxy benzophenone (also known as oxybenzone) can be used. Octyl methoxycinnamate and 2-hydroxy-4-methoxy benzophenone are commercially available under the trade marks, Parsol® MCX and Benzophenone-3, respectively. Ecamsule®, a benzylidene camphor derivative, and drometrizole trisiloxane, a benzotriazole, may also be used. Further examples include Octocrylene, phenylbenzimidazole sulfonic acid (also known as Ensulizole®), ethylhexyl salicylate, diethylhexyl naphthylate, bimotrizinole (trade marked as Tinosorb® S) and bisoctrizole (Tinosorb® M). Inorganic sunscreens include oxides like titanium dioxide and zinc oxide which reflect or scatter the sunrays. The quantity of sunscreens present in the compositions could vary depending upon the degree of protection desired from UV radiation. Preferably, the compositions comprise 0.01 to 15% by weight, more preferably 0.1 to 10 and most preferably 0.5 to 7.5% by weight sunscreen.

Illustrative examples of the types of fragrances that may be used include those comprising terpenes and terpene derivatives like those described in Bauer, K., et al., Common Fragrance and Flavor Materials, VCH Publishers (1990). Further examples include myrcene, dihydromyrenol, citral, tagetone, cis-geranic acid, citronellic acid, mixtures thereof.

The carrier acts as diluent or dispersant for the ingredients of the compositions. The carrier may be aqueous-based, anhydrous or an emulsion, whereby a water-in-oil or oil-in-water emulsion is generally preferred. If the use of water is desired, water typically makes up the balance of the composition, which most preferably is from 40 to 80% by weight of the composition.

In addition to water, organic solvents may optionally be included as carrier to assist any other carrier in the compositions of the present invention. Examples include alkanols like ethyl and isopropyl alcohol.

Other suitable organic solvents include ester oils like isopropyl myristate, cetyl myristate, 2-octyldodecyl myristate, avocado oil, almond oil, olive oil and neopentylglycol dicaprate. Typically, such ester oils assist in emulsifying the compositions, and an effective amount is often used to yield a stable, and most preferably, water-in-oil emulsion.

Emollients may also be used, if desired, as a carrier. Alcohols like 1-hexadecanol (i.e. cetyl alcohol) are preferred. Other emollients include silicone oils and synthetic esters. Silicone oils suitable for use include cyclic or linear polydimethylsiloxanes containing from 3 to 9, preferably from 4 to 5 silicon atoms. Non-volatile silicone oils useful as emollients include polyalkyl siloxanes, polyalkylaryl siloxanes and polyether siloxane copolymers. The non-volatile polyalkyl siloxanes useful polydimethylsiloxanes. Silicone elastomers may also be used. The ester emollients that may optionally be used are:

(i) alkenyl or alkyl esters of fatty acids having 10 to 20 carbon atoms. Examples thereof include isoarachidyl neopentanoate, isononyl isonanonoate, oleyl myristate, oleyl stearate, and oleyl oleate;
(ii) ether-esters such as fatty acid esters of ethoxylated fatty alcohols;
(iii) polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters;
(iv) wax esters such as beeswax, spermaceti, stearyl stearate and arachidyl behenate; and,
(v) sterols esters, of which cholesterol fatty acid esters are examples.

Emollients, when present, typically make up from 0.1 to 50% by weight of the composition, including all ranges subsumed therein.

Fatty acids having from 10 to 30 carbon atoms may also be included as carriers. Examples of such fatty acids include pelargonic, lauric, myristic, palmitic, stearic, isostearic, oleic, linoleic, arachidic, behenic or erucic acid and mixtures thereof.

Humectants of the polyhydric alcohol type may also be employed in the compositions. The humectant often aids in increasing the effectiveness of the emollient, reduces scaling at the skin surface, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. Other humectants which may be used include hydroxyethyl urea. The amount of humectant may be 0.2 to 25% by weight and preferably from 0.5 to 15% by weight of the composition.

Moisturisation may be improved through use of petrolatum or paraffin. Thickeners may also be utilized as a portion of the carrier in the compositions. Typical thickeners include cross-linked acrylates (e.g. Carbopol® 982), hydrophobically-modified acrylates (e.g. Carbopol® 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, *sclerotium*, carrageenan, pectin and combinations of these gums. Amounts of the thickener may range from 0.001 to 5, optimally from 0.01 to 0.5% by weight of the composition.

Surfactants may also be present. When present, the total amount of surfactants is 2 to 40% by weight, and preferably from 4 to 20% by weight, optimally from 5 to 12% by weight of the composition. The surfactant is selected from the group consisting of anionic, nonionic, cationic and amphoteric actives. Particularly preferred nonionic surfactants are those with a $C_{10-20}$ fatty alcohol or acid hydrophobe condensed with from 2 to 100 moles of ethylene oxide or propylene oxide per mole of hydrophobe; mono- and di-fatty acid esters of ethylene glycol; fatty acid monoglyceride; sorbitan, mono- and di-C8-C20 fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_{8\ to\ 20}$ acyl isethionates, acyl glutamates, $C_{8\ to\ 20}$ alkyl ether phosphates and combinations thereof.

Various other ingredients may also be used in compositions. Actives are defined as skin benefit agents other than emollients and other than ingredients that merely improve the physical characteristics of the composition. Although not limited to this category, general examples include extender pigments such as talcs and silicas, as well as alpha-hydroxy acids, beta-hydroxy acids and zinc salts.

Beta-hydroxy acids include salicylic acid. Zinc oxide and zinc pyrithione are examples of useful zinc salts.

Compositions, especially those containing water, need to be protected against harmful microorganisms. Anti-microbial compounds, such as triclosan, and preservatives may become necessary. Suitable preservatives include alkyl esters of p-hydroxybenzoic acid, hydantoin derivatives, propionate salts, and a variety of quaternary ammonium compounds. Particularly preferred preservatives are methyl paraben, propyl paraben, phenoxyethanol and benzyl alcohol. Preservatives are from 0.1 to 2% by weight of the composition.

The packaging could be a patch, bottle, tube, roll-ball applicator, propellant driven aerosol device, squeeze container or lidded jar.

The invention will be explained in details with the help of non-limiting examples.

EXAMPLES

Example 1: Tyrosinase Assay by Oxidation of DOPA

The (tyrosinase) inhibitory activity of a, b, c and d was measured by oxidation of DOPA.

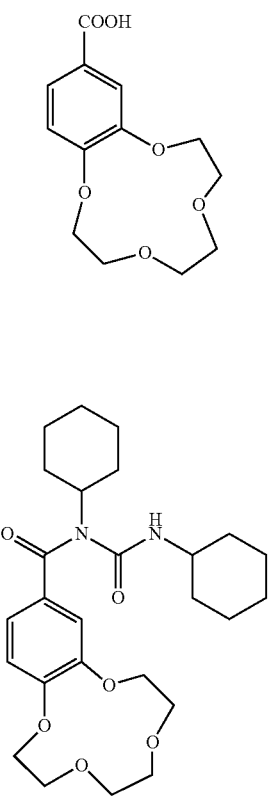

(a)

(b)

(c)

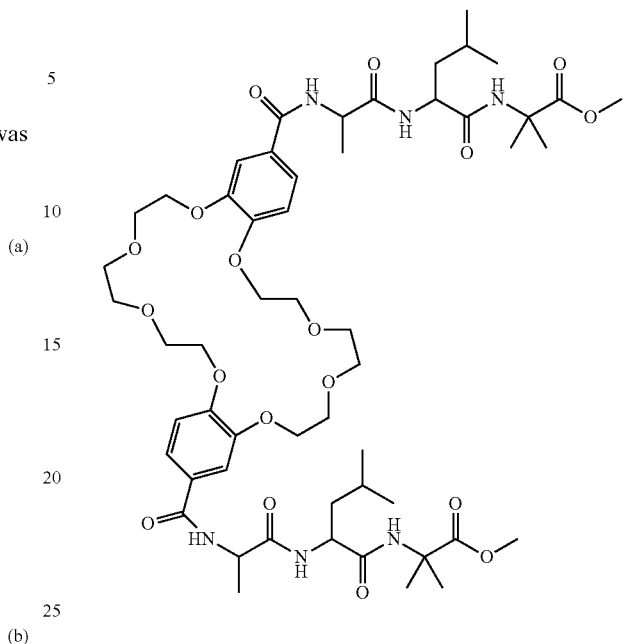

(d)

Each crown ether was tested against human Tyrosinase (in the form of melanocytic extract) and commercial (Worthington, USA) mushroom tyrosinase (MT), using the DOPA oxidation assay. Details of the assay mix are included in table 2.

TABLE 2

| | |
|---|---|
| 0.5M Potassium Phosphate buffer (pH 6.8) | 0.01 ml |
| 3 mM aq. L-DOPA (SIGMA Cat.# D9628) stock | 0.03 ml |
| 2.5 mg/ml human melanocytic lysate OR 1 mg/ml aqueous Mushroom Tyrosinase | 0.002 ml |
| 10 mM test compound stock in 100% DMSO | 0.01 ml |
| Water | 0.048 ml |

Assay examined the change (Optical Density) $OD_{475\,nm}$ at 37° C., after 45 minutes reaction in a standard 96-well plate. All $ON_{475\,nm}$ were corrected by subtracting the background $OD_{475\,nm}$ value of the negative control sample lacking enzyme in the assay mix. The extent of inhibition was calculated using the formula:

$$\% \text{ Inhibition} = 100 * (a/b),$$

where $a=(OD_U - OD_T)$, $b=(OD_U - OD_N)$, U is the uninhibited enzyme alone sample, T is the test compound and N is the no enzyme control.

The observations are summarised in Table 3. The background effect of 10% DMSO on tyrosinase activity was also examined for calculation purposes (i.e. the 'U' sample).

TABLE 3

| Serial No. | Concentration of Test Compound | $OD_{475\,nm}$ (HME) | % Inhibition (HME) | $OD_{475\,nm}$ (MT) | % Inhibition (MT) |
|---|---|---|---|---|---|
| 1 | Uninhibited enzyme positive control | 0.141 | 0 | 0.17 | 0 |
| 2 | 0.5 mM Kojic acid | 0.076 | 46 | 0.084 | 51 |
| 3 | 0.25 mM Kojic acid | 0.100 | 29 | 0.111 | 35 |

TABLE 3-continued

| Serial No. | Concentration of Test Compound | OD$_{475 nm}$ (HME) | % Inhibition (HME) | OD$_{475 nm}$ (MT) | % Inhibition (MT) |
|---|---|---|---|---|---|
| 4 | 0.1 mM Kojic acid | 0.124 | 12 | 0.131 | 23 |
| 5 | 1 mM Compound a | 0.029 | 79 | 0.068 | 60 |
| 6 | 0.1 mM Compound a | 0.126 | 11 | 0.128 | 25 |
| 7 | 1 mM Compound b | 0.162 | No Inhibition | 0.122 | 28 |
| 8 | 0.01 mM Compound b | 0.125 | 12 | 0.160 | 6 |
| 9 | 1 mM Compound c | 0.027 | 81 | 0.087 | 49 |
| 10 | 0.1 mM Compound c | 0.094 | 33 | 0.162 | 5 |
| 11 | 0.01 mM Compound c | 0.092 | 35 | 0.156 | 9 |
| 12 | 1 mM Compound d | 0.110 | 23 | 0.053 | 69 |
| 13 | 0.1 mM Compound d | 0.134 | 5 | 0.071 | 58 |
| 14 | 0.01 mM Compound d | 0.144 | No Inhibition | 0.137 | 19 |

Note:
MT = mushroom tyrosinase,
MHE = human tyrosinase

The data in Table 3 indicates that compound a, b, c and d showed at least 10% inhibition of melanin compared to a vehicle control. It corresponds to inhibition of the activity of tyrosinase (at least one of human or mushroom tyrosinase).

Kojic acid (0.5 mM) inhibits to the extent of 46%.

A compound that inhibits colour by more than 10% of the control value is a tyrosinase inhibitor. The data indicates that compounds a, b, c and d do inhibit the activity of at least one of human or mushroom tyrosinase, in accordance with the assay.

The illustrated examples indicate that exemplified compounds of the formula (I), (IIA) or (IIB) inhibit the activity of tyrosinase in at least one of an animate or inanimate substrate containing tyrosinase.

The invention claimed is:

1. A method for treating hyperpigmentation of human skin by inhibiting the activity of human tyrosinase in human skin, the method comprising contacting said human skin with a compound of formula (I), (IIA) or (IIB):

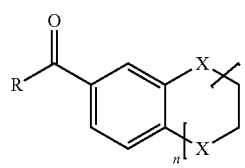
(I)

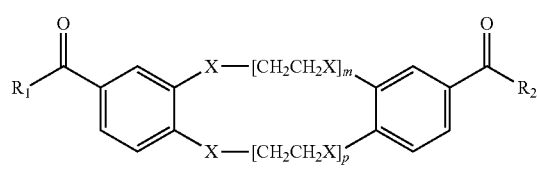
(IIA)

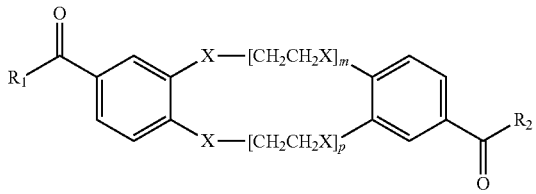
(IIB)

wherein:
X is oxygen;
R is —OH, alkyl, aryl, or peptide group, or a group of formula (III):

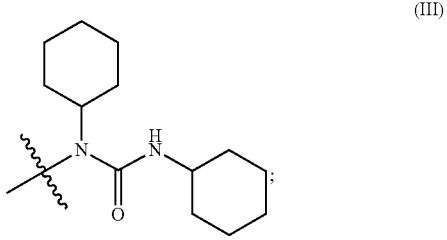 [SMILES: *N(C(=O)NC1CCCCC1)C1CCCCC1]
(III)

$R_1$ is —OH, alkyl, aryl or peptide group;
$R_2$ is —OH, alkyl, aryl or peptide group;
n is an integer from 2 to 5;
m is an integer from 2 to 4; and
p is an integer from 2 to 4.

2. The method as claimed in claim 1 wherein in said formula (I), said R is —OH.

3. The method as claimed in claim 1 wherein in said formula (I), said R is a group of formula (III):

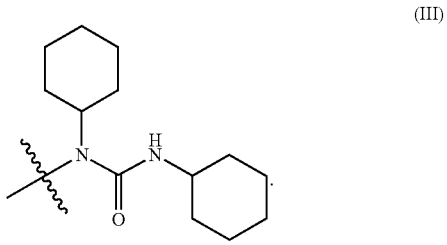 [SMILES: *N(C(=O)NC1CCCCC1)C1CCCCC1]
(III)

4. The method as claimed in claim 1 wherein in said formula (IIA) and (IIB), at least one of said $R_1$ or $R_2$ is —OH.

5. The method as claimed in claim 1 wherein in said formula (IIA) and (IIB), at least one of said $R_1$ or $R_2$ is a group of formula (IV):

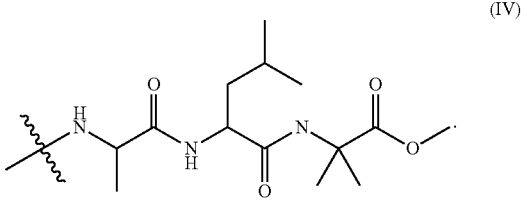 [SMILES: *NC(C)C(=O)NC(CC(C)C)C(=O)NC(C)(C)C(=O)OC]
(IV)

6. The method as claimed in claim 1, wherein the compound of the formula (I), (IIA) or (IIB) is contained in a cosmetic composition.

7. A method for inhibiting the activity of mushroom tyrosinase in a food or beverage composition, the method comprising contacting said food or said beverage composition with a compound of formula (I), (IIA) or (IIB):

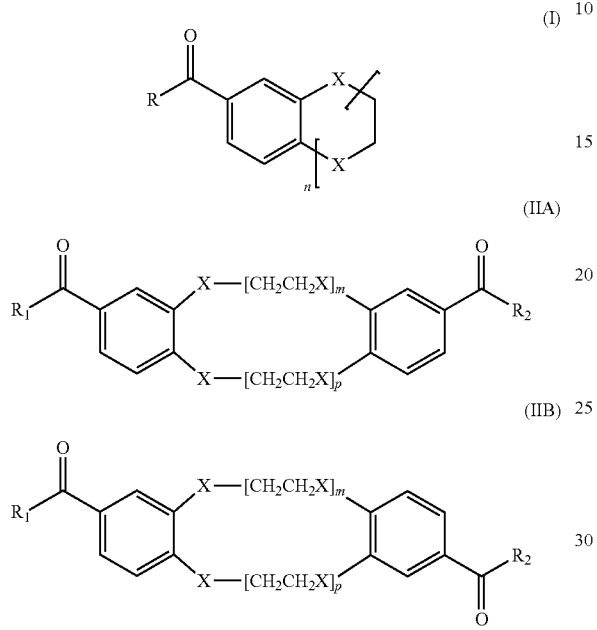

wherein:

X is oxygen;

R is —OH, alkyl, aryl, or peptide group, or a group of formula (III):

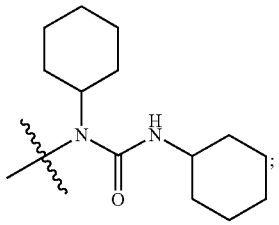

$R_1$ is OH, alkyl, aryl or peptide group;

$R_2$ is —OH, alkyl, aryl or peptide group;

n is an integer from 2 to 5;

m is an integer from 2 to 4; and p is an integer from 2 to 4.

8. The method claimed in claim 1 comprising:

(i) 0.01 to 10% by weight a compound of the formula (I), (IIA), or (IIB); and (ii) a carrier.

* * * * *